United States Patent [19]

Alberto et al.

[11] Patent Number: 5,189,034

[45] Date of Patent: Feb. 23, 1993

[54] BENZOXAZINONE AND BENZOTHIAZINONE DERIVATIVES ENDOWED WITH CARDIOVASCULAR ACTIVITY

[75] Inventors: Sala Alberto, Monza; Francesca Benedini, Milan; Roberta Cereda, Cernusco Lombardone; Piero Del Soldato, Monza, all of Italy

[73] Assignee: Italfarmaco S.P.A., Milan, Italy

[21] Appl. No.: 804,396

[22] Filed: Dec. 10, 1991

[30] Foreign Application Priority Data

Dec. 14, 1990 [IT] Italy ............... 22394

[51] Int. Cl.$^5$ ............... A61K 31/54; A61K 31/535; C07D 279/16; C07D 265/12
[52] U.S. Cl. ............... 514/224.2; 514/230.5; 544/50; 544/92
[58] Field of Search ............... 544/50, 92; 514/224.2, 514/230.5

[56] References Cited

U.S. PATENT DOCUMENTS

| | | | |
|---|---|---|---|
| 3,459,748 | 8/1969 | Krapcho | 544/92 |
| 3,513,166 | 5/1970 | Richman | 544/92 |
| 5,071,850 | 12/1991 | Rieu | 9/89 |

FOREIGN PATENT DOCUMENTS

| | | |
|---|---|---|
| 0171977 | 2/1986 | European Pat. Off. . |
| 1274553 | 5/1972 | United Kingdom . |

OTHER PUBLICATIONS

Tashikawa et al. Chemical Abstracts 94:56841 (1981) Abstr. of Heterocycles (1981) 15(1) 427–430.

Robapharm A. G. Chemical Abstracts 60:530e (1963) Abstr. of FR 1,330,365 Jun. 21, 1963.
Krapcho et al., "Synthesis & Pharmaceutical Activity of Compounds . . . (Thiazesin)" Journal of Medicinal Chem. 11(2) (1968) 361–364.
Fessenden et al., "Organic Chemistry" 2nd ed. p. 282 (1982).
Abstract, 1-Pharmacodynamics, vol. 77, (1972), p. 77, No. 745m.
Chemical Abstracts, vol. 79, (1973), No. 73744m & 73745n, p. 40.

*Primary Examiner*—Mukund J. Shah
*Assistant Examiner*—Matthew V. Grumbling
*Attorney, Agent, or Firm*—Oblon, Spivak, McClelland, Maier & Neustadt

[57] ABSTRACT

Benzoxazinone and benzothiazinone derivatives of formula

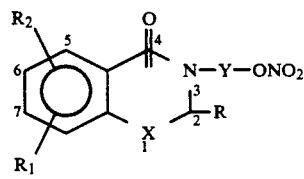

wherein R represents hydrogen, $(C_{2-6})$alkyl, $(C_{5-7})$cycloalkyl, phenyl, substituted phenyl; $R_1$ and $R_2$ independently represents hydrogen, halogen, $(C_{1-4})$alkyl, $(C_{1-4})$alkoxy or trifluoromethyl; X is oxygen or sulfur; Y is $(C_{2-6})$alkylene or $(C_{5-7})$cycloalkylene; and salts therewith of pharmaceutically acceptable acids. The compounds possess cardiovascular activity with high specificity for the coronary district.

9 Claims, No Drawings

BENZOXAZINONE AND BENZOTHIAZINONE DERIVATIVES ENDOWED WITH CARDIOVASCULAR ACTIVITY

The present invention relates to 2,3-dihydro-4H-1,3-benzoxazin-4-ones and 2,3-dihydro-4H-benzothiazin-4-ones of general formula

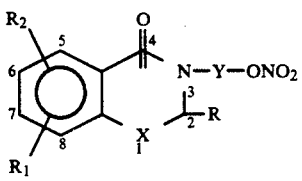

wherein R is hydrogen, ($C_{1-6}$)alkyl, cyclopentyl, cyclohexyl, cycloheptyl, phenyl optionally substituted with 1 or 2 groups independently selected from hydroxy, halogen, nitro, ($C_{1-4}$)alkyl and ($C_{1-4}$)alkoxy, methylenedioxyphenyl; $R_1$ and $R_2$ independently represent hydrogen, halogen, ($C_{1-4}$)alkyl, ($C_{1-4}$)alkoxy or trifluoromethyl; X is an oxygen or a sulfur atom, Y represents a ($C_2$-$C_6$) alkylene chain or a cyclopentylene, cyclohexylene or cycloheptylene moiety; and the pharmaceutically acceptable acid salts thereof. As intended hereinbelow, the alkyl groups essentially identify methyl, ethyl, propyl, i-propyl, butyl, 2-methylpropyl, n-pentyl, 3-methylbutyl, i-pentyl, n-hexil, 2-methylhexyl, 3-methylhexyl and the like, whereas the alkoxy groups are preferably selected from methoxy, ethoxy, propoxy, i-propoxy, butoxy, 2-methylbutoxy and tert.-butoxy. A ($C_{2-6}$)alkylene chain may be linear or branched, and is represented by ethylene, 2-methylethylene, 1,3-propylene, 1,4-butylene 2-ethylethylene, 2-methylpropylene, 1,5-pentylene, 2-ethylpropylene, 2-methylbutylene, 1,6-hexylene, 1-ethyl-1-methylpropylene, 3-methylpentylene and the like.

A preferred group of compounds comprises those compounds of formula I wherein R is hydrogen, ($C_{1-4}$)alkyl, cyclopentyl, cyclohexyl or cycloheptyl, $R_1$ and $R_2$ independently represent hydrogen, halogen, ($C_{1-4}$)alkyl or ($C_{1-4}$)alkoxy, X is an oxygen or a sulfur atom and Y represents a ($C_{2-6}$)alkylene chain or a cyclopentylene, cyclohexylene or cycloheptylene moiety; and the pharmaceutically acceptable salts thereof.

A most preferred group of compounds comprises those compounds of formula I wherein R is hydrogen, $R_1$ and $R_2$ independently represent hydrogen, halogen, ($C_{1-4}$)alkyl or ($C_{1-4}$)alkoxy, X is an oxygen or a sulfur atom and Y is a ($C_{2-6}$)alkylene chain, and the pharmaceutically acceptable salts thereof. N-unsubstituted 2,3-dihydro-4H-1,3-benzoxazin-4-ones were described by B. W. Horrom et al., J. Org. Chem., 72, 721 (1950). This article reports that 2,3-dihydro-2-phenyl-4H-1,3-benzoxazin-4-one is endowed with analgesic activity. Other 2,3-dihydro-4H-1,3-benzoxazin-4-ones were described by R. B. Gammil, J. Org. Chem., 46, 3340 (1981).

Derivatives of the same heterocycle, but bearing substituents also on the nitrogen atom, were described by J. Finkelstein et al., J. Med. Chem., 11, 1038 (1968); they seem to possess anti-inflammatory activity. Finally, analogous derivatives bearing an amino group at the 6-position, still having anti-inflammatory activity, are reported by F. Fontanini et al., Riv. Farmacol. Ter., 4(1), 119 (1973) (Chem. Abs. 73745n Vol.79, page 40, 1973).

The compounds of the invention ar prepared according to a process comprising, as the first step, the formation of a 2,3-dihydro-1,3-benzoxazine or 2,3-dihydro-1,3-benzothiazine derivative of formula

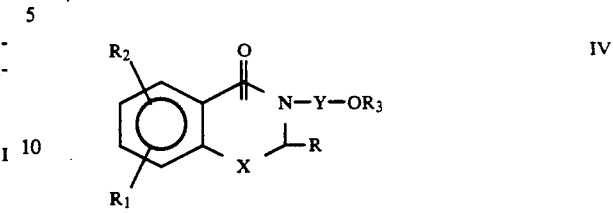

wherein R, $R_1$, $R_2$, X and Y have the above meanings, and $R_3$ is hydrogen or a ($C_{2-4}$)acyl group, by condensing a salicylamide of formula

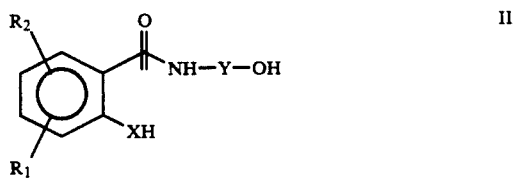

wherein $R_1$, $R_2$, X and Y are as defined above, with an aldehyde of formula $$R-CHO \qquad III$$

wherein R has the above meanings, or with a derivative or precursor thereof.

The condensation usually occurs in an acidic medium, e.g. in a system formed by a strong mineral acid and acetic acid, whereby compounds of formula IV are obtained wherein $R_3$ is acetyl, or by means of molecular sieves in the presence of sulfonic acids such as, for example, p-toluenesulfonic acid, methanesulfonic acid, α- and β-naphthalenesulfonic acid, phosphoric acids, esters and analogous compounds thereof.

The use of molecular sieves is preferred when $R_1$ and/or $R_2$ represent ($C_{1-4}$)alkoxy group, in order to avoid the formation of reaction by-products, difficult to be eliminated.

The condensation is carried out in the presence of an organic solvent, preferably an inert organic solvent such as, for example, benzene, toluene, nitrobenzene or chlorobenzene, halogenated aliphatic hydrocarbons such as methylene chloride, chloroform, 1,2-dichloroethane or 1,1,2-trichloroethylene, cyclohexane, tetrahydrofurane, dimethylformamide, dimethylacetamide, and the like.

The reaction temperature may vary within a quite range without prejudice for the reaction course. The preferred temperature range is comprised between about −10° C. and the reflux temperature of the reaction mixture; the reaction is completed in a time period varying from about 2 to about 30 hours.

The molar amounts of the ragents of formula II and III are not critical for the good progress of the cyclization, as such reagents can be employed in the widest reciprocal stoichiometric ratios. When 2,3-dihydro-4H-1,3-benzoxazinones or -benzothiazinones wherein R is hydrogen or methyl are desired, precursors of the compound of formula III, such as paraformaldehyde and paraldhyde, are preferably employed.

The 2,3-dihydro-1,3-benzoxazine or -benzothiazine derivatives of formula IV wherein $R_3$ is ($C_{2-4}$)acyl are then converted into the desired compounds of formula I as shown in the following reaction scheme

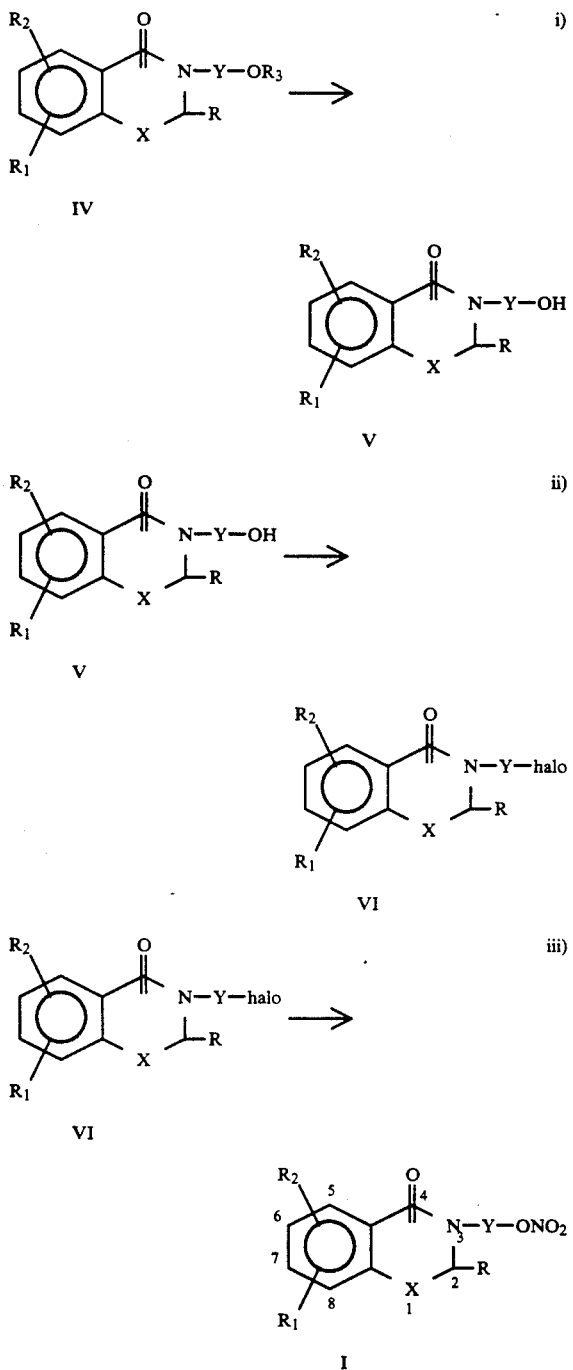

wherein R, $R_1$, $R_2$, X and Y are as defined above and halo is a halogen atom.

It is apparent to the skilled in the art that when a compound of formula IV wherein $R_3$ is hydrogen is obtained by condensing compounds of formulas II and III, it is directly submitted to step ii) of scheme 1 above. Thus, according to step i) of scheme 1, the compounds of formula IV are converted into the compounds of formula V by hydrolysis in an aqueous, alcoholic or aqueous/alcoholic alkaline environment, for example by treatment with an alkaline or alkali-earth metal carbonate or hydrogencarbonate in methanol or ethanol at room temperature for about 10–15 hours. The free OH group of the compounds of formula V is then replaced by a halogen atom by means of common halogenating agents such as, for example, thionyl chloride, sulfuryl chloride, phosphorous trichloride, phosphorous pentachloride, phosphorous oxytrichloride, phosphorous tribromide, sulfuryl bromide and the like. The reaction proceeds in an organic solvent, preferably inert organic solvent again selected from those above employed in the formation of the heterocycle of formula IV, at a temperature varying between about the room temperature and the reflux temperature of the reaction mixture. Thus, compounds of formula VI are obtained, which are subsequently converted into the desired compounds of formula I by procedures suitable for the introduction of the $-ONO_2$ group, for example by treatment with silver nitrate in the presence of an inert organic solvent such as acetonitrile. Preferably, a molar excess of silver nitrate is used, calculated over the compound of formula VI, and the reaction is carried out at a temperature between the boiling temperature of the reaction mixture and the room temperature. The reaction is completed in a time period ranging from about 2 to about 6 hours. The desired final products of formula I are then recovered according to common techniques.

A stated above the compounds of the invention possess a cardiovascular activity. In particular they showed marked vasorelaxing properties in vitro and remarkable vasodilating and antianginal activity when tested in the laboratory animals. These favorable biologic properties are combined with a neglegible hypotensive effect, being it known that this is an undesired side-effect of the nitroderivatives known and employed in therapy.

Furthermore it was surprisingly found that the vasodilating activity of the present compounds is specific for the coronaric conductive vessels. Thus the compounds of the invention may be considered as drugs endowed with potentially coronodilating and specific antianginal actions. Also, they showed to possess antiarrhythmic activity, and this is a further favorable property because the anginal attacks are often associated with more or less marked arrhythmias.

The in vitro vasorelaxing activity was determined by the test of the rabbit aorta strip contracted with noradrenaline. The test was carried out according to the method described by K. Murakami et al., Eur. J. Pharmacol., 141, 195 (1987).

The $IC_{50}$ values i.e., the concentrations of active substances, causing a 50% inhibition of the contraction of the rabbit strip, were determined. The results obtained with some compounds representative of the invention are set forth in the following Table 1

TABLE 1

| Compound of Example | Vasodilative activity in vitro $IC_{50}$ Mole/l |
|---|---|
| 1 | $9.4 \times 10^{-8}$ |
| 2 | $5.4 \times 10^{-9}$ |
| 3 | $6.3 \times 10^{-9}$ |
| 4 | $7.5 \times 10^{-8}$ |
| 7 | $8.8 \times 10^{-9}$ |
| 8 | $1.9 \times 10^{-8}$ |
| 9 | $1.4 \times 10^{-8}$ |
| 10 | $1.7 \times 10^{-8}$ |

The antianginal activity in vivo was determined on anesthetized Sprague Dawley rats of weight 350–400 g, operating according to the method of M. Leitold et al., Arzeim. Forsch., 36, 1454, (1986). The test was carried out by intravenously administering the animals with one I.U/Kg, equivalent to 3 mg/Kg of Arg-vasopressin, thus inducing a coronaric spasm that is reproducible and may be electrocardiographically monitored by an increase of the T-wave. The compounds of the invention were administered by gastric gavage at a dose of 3 mg/Kg one 10 hour before the administration of Arg-vasopressin. The antianginal effect was expressed as the percentage inhibition of the increase of the T-wave versus the controls. Another group of animals were intravenously administered with 4 increasing doses of the compound of the invention to measure their $ED_{50}$, i.e. the dose yielding the 50% inhibition of the increase of the T-wave.

The results obtained for some compounds representative of the invention ar set forth in Table 2 and Table 3.

TABLE 2

| Example | % Inhibition of the increase of the T-wave versus the controls (3 mg/Kg per os) |
|---|---|
| 1 | 55 |
| 3 | 31 |
| 4 | 31 |

TABLE 3

| Example | $ED_{50}$ (mg/Kg) (i.v.) |
|---|---|
| 1 | 0.0013 |
| 2 | 0.0063 |
| 3 | 0.011 |
| 4 | 0.012 |
| 7 | >0.1 |
| 8 | 0.058 |

The above mentioned favorable biological properties are also accompanied by a low toxicity. In fact the $LD_{50}$ values determined according to the method of Lichtfield and Wilcoxon, J. Pharm. Expt. Ther., 96, 99 (1949) are higher than 500 mg/Kg i.p. in mouse and 800 mg/Kg per os in rat.

Object of the present invention is also the use of the new compounds as antianginal agents, in connection with the industrially applicable acts and aspects of said use, comprising their incorporation into pharmaceutical compositions. Examples of such pharmaceutical compositions are tablets, sugar and film coated tablets, syrups and vials, the latter being suitable both for oral and intramuscular or intravenous administration. They contain the active substance alone or in combination with the usual pharmaceutically acceptable carriers and excipients.

The dosages of active substance employed to combat the anginal attacks may vary within wide limits according to the kind of compound used and they are chosen to ensure the most effective therapeutic coverage along the 24 hours.

The starting amides of formula II are known substances or may be prepared as shown in the examples hereinbelow reported, from the corresponding salicylates or thiosalicylates of formula

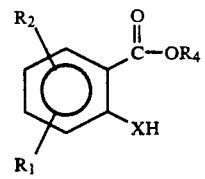

wherein $R_1$, $R_2$ and X have the above mentioned meanings, and $R_4$ is a $C_1$-$C_4$ alkyl, preferably methyl. In turn the compounds of formula VII are known from the literature or are synthesized according to procedures well known to the skilled artisan, starting from the corresponding salicylic and thiosalicylic acids.

The aldehydes of formula III, the derivatives and precursors thereof, are commercial products, or are prepared according to methods known from the literature.

The $^1$H-NMR spectra were recorded in dimethylsulfoxide (DMSO) with a VARIAN GEMINI 200 spectrometer. The $^{13}$C-NMR spectra were recorded by using a VARIAN GEMINI 200 spectometer, taking the dimethylsulfoxide (DMSO) 39.5 ppm peak as the reference peak.

The invention may be better illustrated by the following examples, which, in no way must be construed as a limitation of the scopes of the same.

PART A

Preparation of the Amides of Formula II

Compound 1 N-(2'-Hydroxyethyl)-salicylamide

This compound was prepared as described in Aust. J. Chem., 25, 1797 (1972).

Compound 2 - N-(2'-Hydroxyethyl)-5-methyl-salicylamide 8.5 g of methyl 5-methyl-salycylate (J. Chem. Soc., 61, 1961) in 3.7 ml of 2-aminoethanol were heated at 170° C. for 3 hours. After cooling to room temperature, the reaction mixture was taken up with ethylacetate, washed with 5% hydrochloric acid and dried over sodium sulfate. Yield: 9 g M.p. 73°–75° C. (n-hexane).

Compound 3 - 4-Chloro-N-(2'-hydroxyethyl)-salicylamide

The compound was prepared following the procedure of the previous example starting from 20 g of methyl 4-chlorosalicylate (Chem. Abs. 81, 3624 q) and 8 ml of 2-aminoethanol. Yield: 11 g M.p. 95°–97° C. (chloroform).

Compound 4 - N-(2'-Hydroxyethyl)-4-methylsalicylamide

The compound was prepared following the procedure employed for the preparation of Compound 2 starting from 20 g of methyl 4-methylsalicylate (Chem. Abs. 64, 6568 d) and 9 ml of 2-aminoethanol. Yield: 16.7 g M.p. 78°–80° C. (n-hexane).

Compound 5 - 5-Chloro-N-(2'-hydroxyethyl)-salicylamide

The compound was prepared following the procedure employed for the preparation of Compound 2 starting from 19 g of methyl 5-chlorosalicylate (Arch. Pharm. 296(10), 714, 1963) and 7.5 ml of 2-aminoethanol. Yield: 13.8 g M.p. 100°–102° C. (n-hexane).

Compound 6 - N-(5'-Hydroxypentyl)salicylamide

The compound was prepared following the procedure employed for the preparation of Compound 2 starting from 17.6 g of salicylic acid methyl ester and 8.5 ml of 5-aminopentanol. Yield: 11 g.

The compound is an oil and is used as such in the preparation of the compound of Example 8, PART B.

Compound 7 - N-(2'-Hydroxyethyl)-4-methoxysalicylamide

The compound was prepared following the procedure employed for the preparation of Compound 2 starting from 16.9 g of methyl 4-methoxysalicylate (J. Org. Chem., 23, 756, 1958) and 7 ml of 2-aminoethanol. Yield: 9.5 g M.p. 92°–94° C. (n-hexane).

Compound 8 - N-(2-hydroxyethyl)-2-mercaptobenzamide

A solution of 5 g (0.03 mole of methyl thiosalicylate (Synthesis, 1974) in 4 ml (0.06 mole) of ethanolamine was heated to 140° C. while distilling off the formed methanol. After 2 hours the solution was poured into water and extracted with ethyl acetate. After anhydrification and evaporation under vacuum of the organic layer, 4.2 g (0.01 mole) of bis-[2-(2-hydroxy-ethyl)carboxamidophenyl]disulfide were obtained and as such dissolved in 32 ml of ethanol. The solution was heated to 65° C. and dropwise added with 0.4 (0.01 mole) of sodium borohydride in 21 ml of ethanol. The temperature of the solution was maintained at 65° C. for 1 hour and then brought to room temperature. The residue obtained by evaporation of the solvent was chromatographed on silica gel by eluting with ethyl acetate. 1.4 g of the title compound were obtained as an oil having the following characteristics:

| Elemental analysis | C % | H % | N % | S % |
| --- | --- | --- | --- | --- |
| Calculated | 54.80 | 5.62 | 7.10 | 16.25 |
| Found | 54.78 | 5.60 | 6.91 | 16.19 |

PART B

Preparation of the Compounds of Formula I

EXAMPLE 1

2,3-Dihydro-3-(2'-nitrooxyethyl)-4H-1,3-benzoxazin-4-one

A) A solution of 18.5 g (0.102 mole) of Compound 1 in 500 ml of chloroform and 11 ml of glacial acetic acid was added with 5.5 g of paraformaldehyde. The mixture was cooled to 0° C. and added with 10 g of gaseous hydrochloric acid in 30 minutes, and the resulting solution was stirred at room temperature for 24 hours. The formed oily layer was discarded and the chloroform layer was washed with water and dried over sodium sulfate. The crude residue obtained after evaporation of the solvent was purified by silica gel column chromatography by eluting with methylene chloride/acetone=85/15 (v/v). 13 g of 3-(2'-acetoxyethyl)-2,3-dihydro-4H-1,3-benzoxazin-4-one were recovered. M.p. 49°–51° C. (acetone).

B) A solution of 13 g (0.055 mole) of the compound prepared under A), in 230 ml of methanol was added with 2.75 g (0.026 mole) of sodium carbonate, and the resulting mixture was left at room temperature for 12 hours. The crude residue obtained after evaporation of the solvent was taken up with methylene chloride and the resulting organic layer was washed with water and dried over sodium sulfate. After evaporation of the methylene chloride, 9.5 g of 2,3-dihydro-3-(2'-hydroxyethyl)-4H-1,3-benzoxazin-4-one were obtained. M.p. 59°–61° C. (methylene chloride/acetone=1/9 v/v).

C) The product obtained under B) (9 g, 0.046 mole) was dissolved in 70 ml of chloroform, and the resulting solution was added dropwise with 3.54 ml (0.048 mole) of thionyl chloride. The whole was heated at 70° C. for 3 hours. After washing with 5% sodium hydrocarbonate and water, drying over sodium sulfate, and subsequent evaporation of the solvent, 9.3 g of 3-(2'-chloroethyl)-2,3-dihydro-4H-1,3-benzoxazin-4-one were obtained. M.p. 45°–° C. (n-hexane).

D) The product obtained under C) (5.0 g, 0.023 mole) was dissolved in 50 ml of acetonitrile, and the resulting solution was added with 6 g (0.035 mole) of silver nitrate in 35 ml of acetonitrile. The reaction mixture was heated at 85° C. for 2 hours and then cooled to room temperature. The formed salts were removed by filtration and the solvent was evaporated off. The crude product obtained was taken up with methylene chloride, the organic layer was washed with water and dried over sodium sulfate. After evaporation of methylene chloride 4.8 g of the title product were obtained. M.p. 49°–51° C. (n-hexane).

The following compounds were prepared substantially according to the procedures of the different steps A→D shown in Example 1 starting from the convenient salicylamide or thiosalicylamide. Where otherwise indicated, it has to be understood that every compound A is substantially prepared according to procedure A) of Example 1, every compound B substantially according to procedure B) and so on.

EXAMPLE 2

2,3-Dihydro-6-methyl-3-(2'-nitrooxyethyl)-4H-1,3-benzoxazin-4-one

A) 3-(2'-Acetoxyethyl)-2,3-dihydro-6-methyl-4H-1,3-benzoxazin-4-one starting from 8.0 g (0.041 mole) of Compound 2 and 4.0 g of paraformaldehyde. Yield: 6.0 g M.p. 53°–55° C. (n-hexane).

B) 2,3-Dihydro-3-(2'hydroxyethyl)-6-methyl-4H-1,3-benzoxazin-4-one from 6.0 g (0.024 mole) of the previous compound. Yield: 4.2 g M.p. 59°–61° C. (diethyl ether).

C) 3-(2'-Chloroethyl)-2,3-dihydro-6-methyl-4H-1,3-benzoxazin-4-one from 3.6 g (0.017 mole) of the previous compound. Yield: 3.5 g M.p. 86°–88° C. (n-hexane).

D) 2.7 g of the title compound were obtained starting from 3.3 g (0.014 mole) of the previous compound. M.p. 76°–78° C. (diethyl ether/n-hexane=1/9 v/v).

EXAMPLE 3

7-Chloro-2,3-dihydro-3-(2'-nitrooxyethyl)-4H-1,3-benzoxazin-4-one

A) 3-(2'-Acetoxyethyl)-7-chloro-2,3-dihydro-4H-1,3-benzoxazin-4-one from 11 g (0.051 mole) of Compound 3 and 4.5 g of paraformaldehyde. Yield: 9 g M.p. 92°–94° C. (n-hexane).

B) 7-Chloro-2,3-dihydro-3-(2'-hydroxyethyl)-4H-1,3-benzoxazin- 4-one from 8 g (0.030 mole) of the previous compound. Yield: 6.1 g M.p. 104°–106° C. (n-hexane).

C) 7-Chloro-3-(2'-chloroethyl)-2,3-dihydro-4H-1,3-benzoxazin-4-one from 8 g (0.035 mole) of the previous compound. Yield: 6.2 g M.p. 103°–105° C. (diethyl ether).

D) 5.8 g of the title compound were obtained starting from 6 g (0.024 mole) of the previous compound. M.p. 86°–88° C. (n-hexane).

EXAMPLE 4

2,3-Dihydro-7-methyl-3-(2'-nitrooxyethyl)-4H-1,3-benzoxazin-4-one

A) 3-(2'-Acetoxyethyl)-7-methyl-2,3-dihydro-4H-1,3-benzoxazin-4-one from 16 g (0.081 mole) of Compound 4 and 4.5 g of paraformaldehyde. Yield 13 g of oil showing the following characteristics:

| Elemental analysis: | C % | H % | N % |
| --- | --- | --- | --- |
| Calculated | 62.64 | 6.07 | 5.62 |
| Found | 62.27 | 6.03 | 5.58 |

$^1$H-NMR—characteristic resonance peaks are observed at the following δ (ppm): 7.59 (d, 1H); 6.98 (d, 1H); 6.91 (s, 1H); 5.19 (s, 2H); 4.18 (t, 2H); 3.68 (t, 2H); 2.01 (s, 3H)

$^{13}$C-NMR—characteristic resonance peaks are observed at the following δ (ppm): 171.86; 161.73; 156.03; 145.93; 127.61; 123.04; 116.98; 115.55; 79.04; 68.45; 45.28; 18.41

B) 2,3-Dihydro-3-(2'-hydroxyethyl)-7-methyl-4H-1,3-benzoxazin-4-one from 12 g of the previous compound. Yield: 9 g of product as an oil, used as such in the next step.

C) 3-(2'-Chloroethyl)-2,3-dihydro-7-methyl-4H-1 3-benzoxazin-4-one from 4 g of the previous compound. Yield: 3.7 g M.p. 82°–84° C. (n-hexane).

D) 2.5 g of the title product were obtained from 3 g (0.013 mole) of the previous compound. M.p. 89°–91° C. (ethyl acetate/n-hexane=1/9 v/v).

EXAMPLE 5

2,3-Dihydro-2-methyl-3-(2'nitrooxyethyl)-4H-1,3-benzoxazin-4-one

A) 3-(2'-Acetoxyethyl)-2-methyl-2,3-dihydro-4H-1,3-benzoxazin-4-one starting from 18.4 g (0.101 mole) of Compound 1 and 8.13 mg (0.061 mole) of paraformaldehyde. Yield: 6.7 g of an oil having the following characteristics:

| Elemental analysis: | C % | H % | N % |
| --- | --- | --- | --- |
| Calculated | 62.64 | 6.07 | 5.62 |
| Found | 62.35 | 6.01 | 5.47 |

$^1$H-NMR—characteristic resonance peaks are observed at the following δ (ppm): 7.74 (dd, 1H); 7.52 (dt, 1H); 7.17 (t, 1H); 7.02 (d, 1H); 5.70 (q, 1H); 4.22 (t, 2H); 4.63÷3.83 (m, 1H);3.56÷3.23 (m, 1H); 2.05 (s, 3H); 1.56 (d, 3H)

$^{13}$C-NMR—characteristic resonance peaks are observed at the following δ (ppm): 172.04; 161.58; 156.82; 134.68; 127.82; 122.45; 118.02; 116.93; 84.26; 68.10; 45.63; 22.34; 18.22

B) 2,3-Dihydro-3-(2'-hydroxyethyl)-2-methyl-4H-1,3-benzoxazin-4-one from 6 g (0.029 mole) of the previous compound. Yield: 3.8 g of an oily product used as such in the next step.

C) 3-(2'-Chloroethyl)-2,3-dihydro-2-methyl-4H-1,3-benzoxazin-4-one from 3.5 g of the previous compound. Yield: 3.1 g of an oily product used as such in the next step.

D) 2.1 g of title product were obtained starting from 2.5 g of the previous compound. The product is an oil having the following characteristics:

| Elemental analysis | % C | % H | % N |
| --- | --- | --- | --- |
| Calculated | 52.38 | 4.80 | 11.11 |
| Found | 52.07 | 4.75 | 11.03 |

$^1$H-NMR—characteristic resonance peaks are observed at the following δ (ppm) 7.77 (dd, 1H); 7.52 (dt, 1H); 7.12 (t, 1H); 7.02 (d, 1H); 5.72 (q, 1H); 4.70 (t, 2H); 4.12÷3.97 (m, 1H); 3.66÷3.51 (m, 1H); 1.49 (d, 3H)

$^{13}$C-NMR—characteristic resonance peaks are observed at the following δ (ppm) 161.72; 156.83; 134.65; 128.09; 122.77; 118.71; 116.69; 83.68; 71.72; 40.08; 20.6

EXAMPLE 6

2,3-Dihydro-2,7-dimethyl-3-(2'-nitrooxyethyl)-4H-1,3-benzoxazin-4-one

A) 3-(2'Acetoxyethyl)-2,7-dimethyl-2,3-dihydro-4H-1,3-benzoxazin-4-one from 6 g (0.030 mole) of Compound 4 and 2.4 ml (0.018 mole) of paraldehyde. 2.5 g of product were obtained as an oil having the following characteristics:

| Elemental analysis | % C | % H | % N |
| --- | --- | --- | --- |
| Calculated | 63.87 | 6.51 | 5.32 |
| Found | 63.71 | 6.48 | 5.27 |

$^1$H-NMR—characteristic resonance peaks are observed at the following δ (ppm) 7.63 (d, 1H); 6.92 (d, 1H); 6.88 (s, 1H); 5.66 (q, 1H); 4.28 (t, 2H); 4.08÷3.78 (m, 1H); 3.52÷3.22 (m, 1H); 2.35 (s, 3H); 2.02 (s, 3H); 1.52 (s, 3H)

$^{13}$C-NMR—characteristic resonance peaks are observed at the following δ (ppm): 171.79; 161.35; 144.81; 127.75; 124.08; 117.88; 115.57; 84.33; 67.96; 44.82; 21.75; 18.66; 18.14

B) 2,3-Dihydro-3-(2'-hydroxyethyl)-2,7-dimethyl-4H-1,3-benzoxazin-4-one from 2.3 g (0.009 mole) of the previous compound. Yield: 2.1 g of an oil used as such in the next step.

C) 3-(2'-Chloroethyl)-2,3-dihydro-2,7-dimethyl-4H-1,3-benzoxazin-4-one from 3.4 g of the previous compound. Yield: 3.2 g of an oil used as such in the next step.

D) 1.1 g of the title product were obtained starting from 3.1 g of the previous compound. The product is an oil having the following characteristics:

| Elemental analysis | C % | H % | N % |
| --- | --- | --- | --- |
| Calculated | 54.13 | 5.30 | 10.52 |
| Found | 53.97 | 5.25 | 10.43 |

$^1$H-NMR—characteristic resonance peaks are observed at the following δ (ppm) 7.67 (d, 1H); 6.95 (d, 1H); 6.86 (s, 1H); 5.70 (q, 1H); 4.72 (t, 2H); 4.11÷3.98 (m, 1H); 3.64÷3.52 (m, 1H); 2.33 (s, 3H); 1.49 (d, 3H)

$^{13}$C-NMR—characteristic resonance peaks are observed at the following δ (ppm) 161.32; 155.73; 145.70; 127.66; 123.52; 117.28; 115.36; 84.77; 71.47; 40.01; 21.23; 18.59

EXAMPLE 7

5-Chloro-2,3-dihydro-3-(2'-nitrooxyethyl)-4H-1,3-benzoxazin-4-one

A) 3-(2'-Acetoxyethyl)-5-chloro-2,3-dihydro-4H-1,3-benzoxazin-4-one from 13 g (0.060 mole) of Compound 5 and 4.5 g of paraformaldehyde. Yield: 11 g M.p. 93°-95° C. (n-hexane).

B) 5-Chloro-2,3-dihydro-3-(2'-hydroxyethyl)-4H-1,3-benzoxazin-4-one from 10 g (0.037 mole) of the previous compound. Yield: 7 g M.p. 88°-90° C. (diethyl ether).

C) 5-Chloro-3-(2'-chloroethyl)-2,3-dihydro-4H-1,3-benzoxazin-4-one from 8.5 g (0.037 mole) of the previous compound. Yield: 6.5 g M.p. 75°-77° C. (diethyl ether).

D) 3.7 of the title product were obtained starting from 4 g (0.016 mole) of the previous compound. M.p. 98°-100° C. (n-hexane).

EXAMPLE 8

2,3-Dihydro-3-(5'-nitrooxypentyl)-4H-1,3-benzoxazin-4-one

A) N-(5'-Acetoxypentyl)-2,3-dihydro-4H-1,3-benzoxazin-4-one from 11.4 g (0.051 mole) of Compound 6 and 4.5 g of paraformaldehyde. Yield: 9 g of product as an oil having the following characteristic:

| Elemental analysis | C % | H % | N % |
| --- | --- | --- | --- |
| Calculated | 64.97 | 6.91 | 5.05 |
| Found | 64.66 | 6.88 | 5.01 |

$^1$H-NMR—characteristic resonance peaks are observed at the following δ (ppm) 7.79 (dd, 1H); 7.51 (dt, 1H); 7.14 (t, 1H); 7.04 (d, 1H); 5.29 (s, 2H); 4.03 (t, 2H); 3.44 (t, 2H); 2.04 (s, 3H); 1.60÷1.19 (m, 6H)

$^{13}$C-NMR—characteristic resonance peaks are observed at the following δ 8ppm) 171.43; 162.04; 156.23; 134.35; 127.92; 123.01; 118.78; 116.32; 78.12; 68.03; 44.27; 29.72; 28.97; 23.84; 18.13

B) 2,3-Dihydro-3-(5'-hydroxypentyl)-4H-1,3-benzoxazin-4-one from 8.5 g (0.031 mole) of the previous compound. 5.3 g of product as an oil were obtained used as such in the next step.

C) 3-(5'-Chloropentyl)-2,3-dihydro-4H-1,3-benzoxazin-4-one- from 7.3 g of the previous compound. Yield: 4.6 g M.p. 41°-43° C. (n-hexane).

D) 2.5 g of the title product were obtained starting from 8 g (0.031 mole) of the previous compound. M.p. 39°-41° C. (n-hexane).

EXAMPLE 9

2,3-Dihydro-7-methoxy-3-(2'-nitrooxyethyl)-4H-1,3-benzoxazin-4-one

A) 3-(2'-hydroxyethyl)-7-methoxy-2,3-dihydro-4H-1,3-benzoxazin-4-one, 9 g (0.042 mole) of Compound 7 and 0.81 g (0.004 mole) of p-toluensulfonic acid were dissolved in 130 ml of benzene, and 4 Å molecular sieves and 1.55 g of paraformaldehyde were added to the resulting solution. The mixture was refluxed for 2 hours and, after cooling to room temperature, added with 300 ml of ethyl acetate. The molecular sieves were removed by filtration, the solution was washed with water, the organic layer was recovered and dried over sodium sulfate. After evaporation of the solvent, 10.3 g of a residue were obtained which was purified through a silica gel column by eluting with ethyl acetate/n-hexane=8/2 (v/v). Yield: 2.1 g of product as an oil having the following characteristics:

| Elemental analysis | C % | H % | N % |
| --- | --- | --- | --- |
| Calculated | 59.19 | 5.87 | 6.27 |
| Found | 59.01 | 5.84 | 6.21 |

$^1$H-NMR—characteristic resonance peaks are observed at the following δ (ppm) 7.83 (d, 1H); 6.63 (dd, 1H); 6.42 (d, 1H); 5.36 (s, 2H); 4.88 (t, 1H); 3.62÷3.47 (m, 4H); 3.81 (s, 3H)

$^{13}$C-NMR—characteristic resonance peaks are observed at the following δ (ppm) 163.18; 157.36; 154.28; 132.48; 130.76; 115.13; 109.78; 77.39; 59.42; 47.19

C) 3-(2'-Chloroethyl)-2,3-dihydro-7-methoxy-4H-1,3-benzoxazin-4-one from 2 g (0.009 mole) of the previous compound. Yield: 1.9 g of product as oil used as such in the next step.

D) 1.7 of the title product were obtained starting from 2 g (0.008 mole) of the previous compound. M.p. 97°-99° C. (n-hexane).

EXAMPLE 10

3(2'-nitrooxyethyl)-2,3-dihydro-4H-1,3-benzothiazin-4-one

A)
3-(2'-hydroxyethyl)-2,3-dihydro-4H-1,3-benzothiazin-4-one

A solution of 3.5 g (0.017 mole) of the compound 8 in 50 ml of dioxane was added with 1.59 g (0.053 mole) of paraformaldehyde. The solution cooled to 0° C. was saturated with gaseous hydrochloric acid, then brought to room temperature and stirred for 3 days. After dilution with water the reaction mixture was extracted with ethyl acetate. The organic phase was dried over sodium sulfate and evaporated under vacuum and the obtained residue was chromatographed through silica gel (ethyl acetate/hexane 8/2 (v/v) as the eluent). 1.5 g of the title compound was obtained as an oil which was used as such in the subsequent step.

B)
3-(2'-chloroethyl)-2,3-dihydro-4H-1.3-benzothiazin-4-one.

The compound was prepared as described in Example 1C) starting from 1 g (0.0048 mole) of the product obtained under B). 0.980 g of the title compound were obtained as an oil which was used as such in the subsequent step.

C)
3-(2'-nitrooxyethyl)-2,3-dihydro-4H-1,3-benzothiazin-4-one

The compound was prepared as described in Example 1D) starting from 0.700 g (0.003 mole) of the product obtained under C). 0.530 g of the title product were obtained. M.p. 68°-69° C.

| Elemental analysis | C % | H % | N % | S % |
| --- | --- | --- | --- | --- |
| Calculated | 47.24 | 3.96 | 11.02 | 12.61 |
| Found | 47.21 | 3.93 | 11.05 | 12.57 |

$^1$H-NMR in DMSO 7.96 (dd, 1H); 7.52÷7.29 (m, 3H); 4.88 (s, 2H); 4.76 (t, 2H); 3.94 (t, 2H)

The following products of general formula I were prepared according to the methods described in the previous examples starting from the convenient amide and carbonyl compounds, derivatives or precursors thereof.

| Heterocycle (2,3-Dihydro) | —Y—ONO$_2$ | R$_1$ | R$_2$ |
|---|---|---|---|
| 4H-1,3-benzoxazin-4-one | 2'-nitrooxyethyl | hydrogen | 7-trifluoromethyl |
| 4H-1,3-benzoxazin-4-one | " | " | 6-fluoro |
| 4H-1,3-benzoxazin-4-one | " | " | 5-chloro |
| 4H-1,3-benzoxazin-4-one | " | " | 8-methoxy |
| 4H-1,3-benzoxazin-4-one | " | 6-chloro | 7-chloro |
| 4H-1,3-benzoxazin-4-one | " | 5-chloro | 7-chloro |
| 4H-1,3-benzoxazin-4-one | 3'-nitrooxypropyl | hydrogen | hydrogen |
| 4H-1,3-benzoxazin-4-one | " | " | 6-chloro |
| 4H-1,3-benzoxazin-4-one | 4'-nitrooxybutyl | " | hydrogen |
| 4H-1,3-benzoxazin-4-one | " | " | 6-chloro |
| 4H-1,3-benzoxazin-4-one | " | " | 7-methyl |
| 4H-1,3-benzoxazin-4-one | 5'-nitrooxypentyl | " | 6-chloro |
| 4H-1,3-benzoxazin-4-one | " | " | 7-methyl |
| 4H-1,3-benzoxazin-4-one | " | 6-chloro | 7-chloro |
| 2-methyl-4H-1,3-benzoxazin-4-one | 5'-nitrooxypentyl | hydrogen | hydrogen |
| 2-methyl-4H-1,3-benzoxazin-4-one | " | 6-chloro | 7-chloro |
| 2-cyclohexyl-4H-1,3-benzoxazin-4-one | 2'-nitrooxyethyl | hydrogen | hydrogen |
| 2-cyclohexyl-4H-1,3-benzoxazin-4-one | " | " | 6-chloro |
| 2-phenyl-4H-1,3-benzoxazin-4-one | 2'-nitrooxyethyl | " | hydrogen |
| 2-phenyl-4H-1,3-benzoxazin-4-one | " | " | 6-chloro |
| 2-phenyl-4H-1,3-benzoxazin-4-one | " | 6-chloro | 7-chloro |
| 2-(4-chlorophenyl)-4H-1,3-benzoxazin-4-one | 2'-nitrooxyethyl | hydrogen | hydrogen |
| 4H-benzothiazin-4-one | 2'-nitrooxyethyl | hydrogen | 6-chloro |
| " | " | " | 7-chloro |
| " | " | " | 7-methyl |
| " | " | 6-chloro | 7-chloro |
| " | 5'-nitrooxypentyl | hydrogen | hydrogen |
| 2-methyl-4H-1,3-benzothiazin-4-one | 2'-nitrooxyethyl | " | " |

We claim:
1. Compounds of general formula

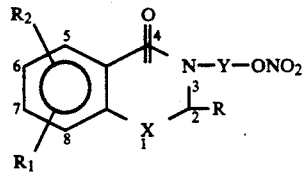

wherein R represents hydrogen, (C$_{1-6}$)alkyl, cyclopentyl, cyclohexyl, or cycloheptyl; R$_1$ and R$_2$ independently represent hydrogen, halogen, (C$_{1-4}$)alkyl, (C$_{1-4}$)alkoxy or trifluoromethyl; X is an oxygen or a sulfur atom, Y represents a (C$_2$-C$_6$)alkylene chain or a cyclopentylene, cyclohexylene or cyclopentylene group; and the pharmaceutically acceptable acid salts thereof.

2. Compounds according to claim 1 wherein R is hydrogen, (C$_{1-4}$)alkyl, cyclopentyl, cyclohexyl or cycloheptyl; R$_1$ and R$_2$ independently represent hydrogen, halogen, (C$_{1-4}$)alkyl or (C$_{1-4}$)alkoxy; X is an oxygen or a sulfur atom and Y represents a (C$_{2-6}$)alkylene chain or a cyclopentylene, cyclohexylene or cycloheptylene moiety; and the pharmaceutically acceptable salts thereof.

3. Compounds according to claim 1 or 2 wherein R is hydrogen, R$_1$ and R$_2$ independently represent hydrogen, halogen, (C$_{1-4}$)alkyl or (C$_{1-4}$)alkoxy; X is an oxygen or a sulfur atom; and Y is a (C$_{2-6}$)alkylene chain; and the pharmaceutically acceptable salts thereof.

4. A compound as defined in claim 1 which is 2,3-dihydro-3-(2'-nitrooxyethyl)-4H-1,3-benzoxazin-4-one.

5. A compound as defined in claim 1 which is 2,3-dihydro-6-methyl-3-(2'-nitrooxyethyl)-4H-1,3-benzoxazin-4-one.

6. A compound as defined in claim 1 which is 2,3-dihydro-7-chloro-3-(2'-nitrooxyethyl)-4H-1,3-benzoxazin-4-one.

7. A compound as defined in claim 1 which is 2,3-dihydro-7-methyl-3-(2'-nitrooxyethyl)-4H-1,3-benzoxazin-4-one.

8. A compound as defined in claim 1 which is 2,3-dihydro-3-(2'-nitrooxyethyl)-4H-1,3-benzothiazin-4-one.

9. A pharmaceutical composition for cardiovascular therapy, comprising a therapeutically effective amount of at least one of the compounds as defined in claim 1 together with at least one pharmaceutically acceptable excipient.

* * * * *

UNITED STATES PATENT AND TRADEMARK OFFICE
CERTIFICATE OF CORRECTION

PATENT NO. : 5,189,034
DATED : February 23, 1993
INVENTOR(S) : Alberto Sala et al.

It is certified that error appears in the above-identified patent and that said Letters Patent is hereby corrected as shown below:

On the title page, Item [19] and Item [75],

The first inventor's name is listed incorrectly, should read as follows:   --[19]  Sala et al.--

--[75]  Alberto Sala--

Signed and Sealed this

Second Day of November, 1993

Attest:

BRUCE LEHMAN

Attesting Officer        Commissioner of Patents and Trademarks

UNITED STATES PATENT AND TRADEMARK OFFICE
CERTIFICATE OF CORRECTION

PATENT NO. : 5,189,034
DATED : FEBRUARY 23, 1993
INVENTOR(S) : SALA ALBERTO ET AL

It is certified that error appears in the above-identified patent and that said Letters Patent is hereby corrected as shown below:

Column 1, line 29, "n-hexil" should read --n-hexyl--.

Column 2, line 54, after "quite", insert --wide--;
line 66, "paraldhyde" should read -- paraldehyde--.

Column 7, line 21, "(Synthesis, 1974)" should read --(Synthesis 59, 1974)--.

Column 8, line 15, "45°-°C" should read --45°-47°C--;
line 45, "(2'hydroxyethyl)" should read --2'-hydroxyethyl--.

Column 9, line 32, "-4H-1 3-" should read -- -4H-1, 3- --.

Signed and Sealed this

Seventh Day of June, 1994

Attest:

BRUCE LEHMAN

*Attesting Officer*  Commissioner of Patents and Trademarks

UNITED STATES PATENT AND TRADEMARK OFFICE
CERTIFICATE OF CORRECTION

PATENT NO. : 5,189,034
DATED : FEBRUARY 23, 1993
INVENTOR(S) : ALBERTO SALA et al

It is certified that error appears in the above-indentified patent and that said Letters Patent is hereby corrected as shown below:

Column 11, line 3, "5-Chloro" should read --6-Chloro--;
           line 5, "5-Chloro" should read --6-Chloro--;
           line 9, "5-Chloro" should read --6-Chloro--;
           line 12, "5-Chloro" should read --6-Chloro--.

Signed and Sealed this

Fifth Day of March, 1996

*Attest:*

BRUCE LEHMAN

*Attesting Officer*     *Commissioner of Patents and Trademarks*